(12) United States Patent
Rubel (10) Patent No.: US 8,608,700 B2
(45) Date of Patent: Dec. 17, 2013

(54) MICROFABICATED ELECTROMAGNETIC ACTUATOR WITH PUSH-PULL MOTION

(75) Inventor: Paul J. Rubel, Santa Barbara, CA (US)

(73) Assignee: Innovative Micro Technology, Goleta, CA (US)

( * ) Notice: Subject to any disclaimer, the term of this patent is extended or adjusted under 35 U.S.C. 154(b) by 222 days.

(21) Appl. No.: 13/067,325

(22) Filed: May 25, 2011

(65) Prior Publication Data

US 2012/0302946 A1 Nov. 29, 2012

(51) Int. Cl.
*A61M 1/00* (2006.01)
(52) U.S. Cl.
USPC .............. 604/151; 604/67; 335/268; 417/480
(58) Field of Classification Search
USPC ...................... 604/65–67, 131, 151; 335/268; 417/480–481
See application file for complete search history.

(56) References Cited

U.S. PATENT DOCUMENTS

| | | | | |
|---|---|---|---|---|
| 5,167,626 | A | * | 12/1992 | Casper et al. .............. 604/891.1 |
| 7,221,247 | B2 | * | 5/2007 | Levitan et al. ................. 335/209 |
| 7,887,508 | B2 | * | 2/2011 | Meng et al. ................... 604/114 |

OTHER PUBLICATIONS

"A Low Voltage Push-Pull SPDT RF MEMS Switch Operated by a Combination of Electromagnetic Actuation and Electrostatic Hold," Il-Joo Cho, et al., IEEE Transactions, pp. 32-35, May 5, 2005.
U.S. Appl. No. 12/801,162, filed May 26, 2010, Foster, et al.

* cited by examiner

*Primary Examiner* — Theodore Stigell
(74) *Attorney, Agent, or Firm* — Jaquelin K. Spong (57) ABSTRACT

A micromechanical electromagnetic actuator may have two separate components: a flux-generating portion and a separate movable structure. The flux-generating portion may have a plurality of conductive coils wound around a magnetically permeable material. Each coil generates a magnetic field along its axis, which is different for each of the coils. The adjacent movable structure may include magnetically permeable features, one inlaid in the movable structure and other stationary features which focus the flux produced by the flux-generating mechanism across a gap between the stationary features. By energizing each coil sequentially, a push-pull motion in the actuator may result from the force of the magnetically permeable features. This push-pull actuator may be particularly effective when used as a pumping element in a drug delivery system, or other fluidic pumping system.

16 Claims, 10 Drawing Sheets

MICROFABRICATED ELECTROMAGNETIC ACTUATOR WITH PUSH-PULL MOTION

CROSS REFERENCE TO RELATED APPLICATIONS

This application is related to U.S. patent application Ser. No. 12/801,162, filed May 26, 2010, which is incorporated by reference in its entirety.

STATEMENT REGARDING FEDERALLY SPONSORED RESEARCH

Not applicable.

STATEMENT REGARDING MICROFICHE APPENDIX

Not applicable.

FIELD OF THE INVENTION

This invention relates to microfabricated actuators. More particularly, this invention relates to a microelectromechanical systems (MEMS) electromagnetic actuators.

BACKGROUND

Microelectromechanical systems (MEMS) are small, generally movable devices which are made using semiconductor integrated circuit fabrication techniques. Because of these batch processing techniques, large numbers of small MEMS devices can be made on a single wafer substrate at low cost with high precision. MEMS devices typically have dimensions on the order of microns, and can thus be used to make very small actuators which are capable of very small and precise movements. Such actuators can make use of any of a number of phenomena to produce motion in the movable member. MEMS actuators are known which use electrostatic, thermal, magnetostatic and piezo electric effects, for example, to produce motion in the movable actuator member.

Microelectromechanical systems (MEMS) techniques may therefore be used to produce microfabricated piezoelectric actuators. Piezoelectric materials are those which undergo a strain when a voltage is applied, or generate a voltage when a stress is applied. Prior art actuators exist which use piezoelectric materials, and may be used as the pumping mechanism for a microfluidic pump. The piezoelectric microactuator can be made by depositing a stack of piezoelectric layers on a thin diaphragm which defines the pumping chamber. Application of a voltage to the piezoelectric stack results in a deformation of the diaphragm, which draws the fluid into the chamber through an inlet valve. When the voltage is discontinued, the diaphragm returns to its original shape, forcing fluid out of the chamber through an outlet valve. Piezoelectric microactuators generally produce a force perpendicular to the plane of the substrate on which they are deposited, and thus move primarily in this direction. A thorough analysis of the attributes of such a pump is set forth in "Simulation of MEMS Piezoelectric Micropump for Biomedical Applications", which discusses the speed and displacement of such an actuator, and can be accessed at http://www.algor.com/news_pub/tech_white_papers/MEMS_micropump/default.asp.

Lead zirconate titanate, Pb(Zr,Ti)O$_3$ (PZT), is a common piezoelectric material that can be deposited on silicon wafers by RF sputtering, for example. However, care must be taken to relieve the stresses in the deposited material in order to avoid static deformation, or warpage, of the pumping diaphragm. Alternatively, high performance PZT wafers are also under development; however they are not yet available in sufficiently large (150 mm round) format to facilitate wafer-to-wafer bonding, an essential process for low cost manufacturing. Accordingly, the exemplary piezoelectric micropump discussed above is an idealized case, with zero residual stress, and such pumps tend to be expensive and difficult to fabricate.

This technology has several other drawbacks, the most significant of which are that the piezoelectric actuator has limited throw and requires large actuation voltages. If non-resonant excitation of the above structure is used to actuate the diaphragm, the displacement of the design described above is less than 10 μm for a 200V input. If resonant excitation is used; i.e. a modulated voltage waveform is applied to the device to amplify the displacement, a ten fold increase in the displacement can be achieved; however, it takes about 100 msec to achieve this displacement. The low resonant frequency is a result of the weight of the piezoelectric material and the size of the pumping diaphragm needed to achieve the necessary pumping volume. The mass of the volume of fluid may also play a role in the low resonant frequency. If the pump is operated above this resonant frequency, the displacement is greatly diminished to only about 3 μm at 500 Hz for 200V input.

Furthermore, when used in a pumping device, the piezoelectric device described above has chambers and a layout that do not allow the passage of relatively large particles. For example, particles in excess of about 10 μm will not pass readily through the fluid path, because of the severe turns and small apertures in the path. Vertical pumps such as that described may also be relatively expensive and difficult to fabricate, because the valves are necessarily formed vertically below the diaphragm using other layers. Finally, since the piezoelectric material can only generate a strain in a single direction in response to an applied voltage, the actuator can only deform in one direction, i.e. it can only "push" and cannot "pull".

Accordingly, a need exists for a microactuator capable of delivering small volumes of fluids as well as particulate matter suspended in the fluid stream, and which is inexpensive and easy to fabricate. The microactuator ideally operates at low voltages and is capable of being powered by a small battery.

SUMMARY

Disclosed herein is a MEMS electromagnetic actuator which can pull as well as push. When deployed as a fluid pump, the actuator is also capable of pumping slurries of particulate matter suspended in a fluid stream. The microactuator may be batch fabricated, and so may be relatively inexpensive and easy to fabricate, and operates at low voltages and powers. Although referred to herein as a "push-pull actuator," it should be understood that this term is intended to refer to an actuator that can move in two substantially different directions in response to a force-generating apparatus. Thus the term does not limit the actuator to one with antiparallel motion.

The electromagnetic actuator may have two separate components: a flux-generating portion and a separate, permeable, movable portion. The movable portion may be formed on a substrate with at least one magnetically permeable feature, and the flux-generating portion, may be formed separate from the substrate. The flux-generating portion generates lines of flux which are collected by the at least one magnetically permeable feature, wherein the flux-generating portion includes a plurality of electrical coils, each of which generates a magnetic field in a substantially different direction, wherein the fields produced by the plurality of coils causes a movement in the movable structure in a plurality of directions. For example, one first set of coils may produce a flux along the axis of the coil in one direction. Another second set of coils disposed perpendicularly to the first will generate flux in the perpendicular direction. The first set of coils may drive the movable portion away from the flux-generating portion, wherein the second set of coils may draw the movable portion toward the flux-generating portion, yielding a push-pull actuator. The operation of this anti-parallel, push-pull electromagnetic actuator is described in detail below.

The movable portion of the push-pull electromagnetic MEMS actuator may be fabricated by forming a magnetically permeable, movable feature affixed to support diaphragm or membrane, using MEMS fabrication techniques, for example. The separate flux-generating portion may be a hand-wound core, for example. The flux-generating portion is then brought into close proximity to the movable portion, such that the two are separated by a narrow gap. Then, a first of the set of conducting coils is energized in the flux-generating portion. This produces flux along the axis of the coil and in the permeable core. The flux circulating in the flux-generating portion jumps across the narrow gap, entering the permeable feature of the movable diaphragm, and provides a magnetic field gradient whose details depends on the orientation and disposition of these permeable features. This field gradient may push the diaphragm back, toward the permeable features and away from the flux-generating portion. The pushing of the diaphragm may be used to expel a fluid from a fluidic chamber, and draw fluid into another fluidic chamber.

The first coil is then disengaged from the power supply, and the other coil is energized, producing a magnetic field along its orthogonal axis. This field may interact differently with the permeable features, and draw the movable portion in a different direction, such as toward the flux-generating portion. This may reduce the volume of the pumping chamber, thus forcing fluid through an outlet valve. This motion may expel fluid from one chamber, and draw fluid into another.

The push-pull electromagnetic actuator moves substantially in the plane of the substrate. For at least this reason, relatively complex structures may be used for the actuator element. For example, restoring springs may have a complex shape, in order to achieve the required spring constant. Thus, the push-pull electromagnetic actuator is relatively inexpensive and easy to fabricate, using MEMS surface micromachining techniques. Furthermore, the push-pull electromagnetic actuator uses electromagnetic actuation, which is capable of generating at least about 3 mN of actuation force and at least 10 um displacement. This actuation force may be sufficient for use as a fluid pump, to force the fluid through a 200 μm aperture cannula. Because of its relatively large pumping force, the push-pull electromagnetic MEMS actuator may be coupled with a cannula or hypodermic needle and drug reservoir, to deliver a drug subcutaneously from a drug reservoir to a patient in need of the drug.

Because the pump displacement is small, the microfabricated pump is capable of delivering dosages in very small, well controlled amounts. Because the power requirements are also small, battery operation with a button-type battery is foreseen. For these reasons, it is anticipated that this pump design may be appropriate for the delivery of small amounts of drugs such as insulin on a nearly continuous basis to a diabetic patient. The push-pull electromagnetic MEMS pump may be designed to fit within an adhesive patch worn against the skin of diabetic patients, such that the device is able to operate in a way that closely mimics the function of the human pancreas. However, potential applications are not limited to diabetes treatments. It may also be used to deliver any of a wide range of medications, including chemotherapies, pain medication and other therapeutic compounds that are best administered in small, controlled dosages. For example, the push-pull electromagnetic MEMS pump may be used for the delivery of nitroglycerin (for chest pain), scopolamine (for motion sickness), nicotine (for smoking cessation), clonidine (for high blood pressure), and fentanyl (for pain relief), as well as hormones (for menopausal symptoms) and many other drugs/applications.

While the push-pull electromagnetic actuator is described with respect to a particular application, that of a fluid pump, it should be understood that the actuator may be applied to many other situations as well. Its reciprocating motion may be adapted to the rotation of a shaft, for example, when coupled with appropriate gears and bearings.

These and other features and advantages are described in, or are apparent from, the following detailed description.

BRIEF DESCRIPTION OF THE DRAWINGS

The present invention will be understood more fully from the following detailed description, and from the accompanying drawings, which however, should not be taken to limit the invention to the specific embodiments shown but are for explanation and understanding only. In the figures, like numbers may refer to the same, or analogous features in the various views.

DETAILED DESCRIPTION

The systems and methods set forth herein are describe a microfabricated actuator which moves substantially in the plane of the device, and can pull in one direction as well as push in another direction. The actuation mechanism may be electromagnetic, wherein magnetic flux generated by a plurality of coils in a flux-generating mechanism which interacts with at least one magnetically permeable feature in a movable portion of the actuator. However, the concepts disclosed here may also be applied to an electrostatic actuator using similar concepts.

The permeable features in the movable portion may be arranged in such a way as to retract the movable member when a first coil is activated. Upon cessation of the current in the first coil and the energizing of a second coil, the second magnetic field may operate to move the movable member in another direction, for example in the opposite direction. The sequential energizing of the one or more coils may thus create a push-pull, anti-parallel or reciprocating motion in the movable member.

The movement of this actuator may change the volumes of a pumping chamber, thus moving fluid through the pumping chamber. By combining the piston or diaphragm with a set of active or passive valves, a microfabricated pump may be realized. Finally, a method for manufacturing the microfabricated actuator is set forth.

Figure 1A:
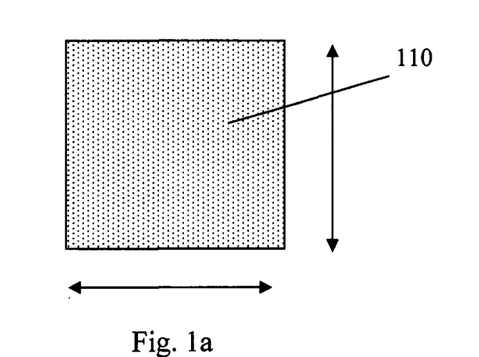
FIGS. 1a-1c is a simplified schematic view of the exemplary construction of the flux-generating portion of a push-pull actuator.

FIG. 1 shows a core of permeable magnetic material 110 which may form the basis of a flux-generating portion 100. The permeable material may be any soft, magnetic material such as an alloy of nickel and iron, e.g. "Permalloy" 60/40, about 60% nickel and 40% iron. Other suitable materials include "Mu-metal" which is about 75% nickel and 25% iron, ferrite or steel. The shape of the material may be approximately square, as shown, or may have other shapes to vary the relative force in the different directions, as described more fully below.

Figure 1B:
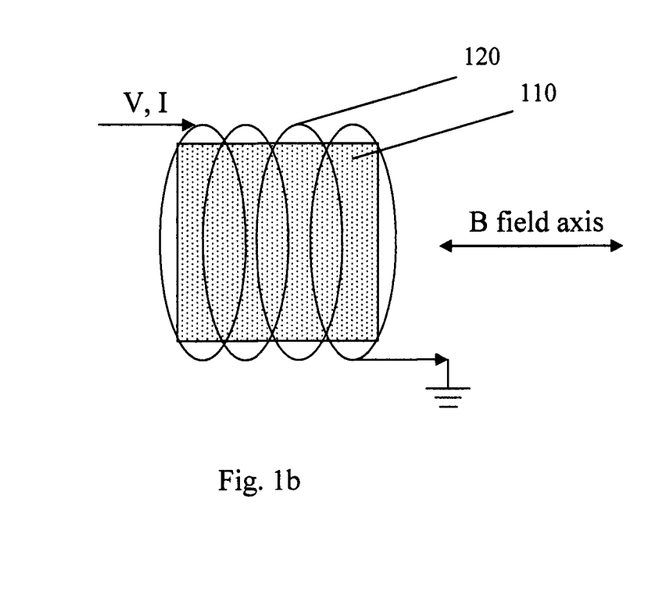

Around the permeable core 110, a coil of conductive material 120 may be wound. When energized, the coil 120 will produce a magnetic field substantially along the axis of the coil 120, and amplified by the permeable material. For example, a copper coil having about 600 turns and carrying about 4 Ampere of current would be sufficient to saturate a permalloy core of dimension 5 mm×5 mm. The coil 120 may be hand wound or machine wound around the core 110.

Figure 1C:
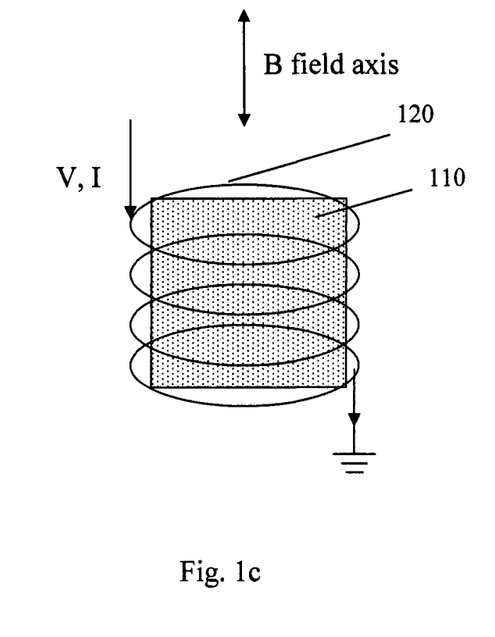
Figure 2:
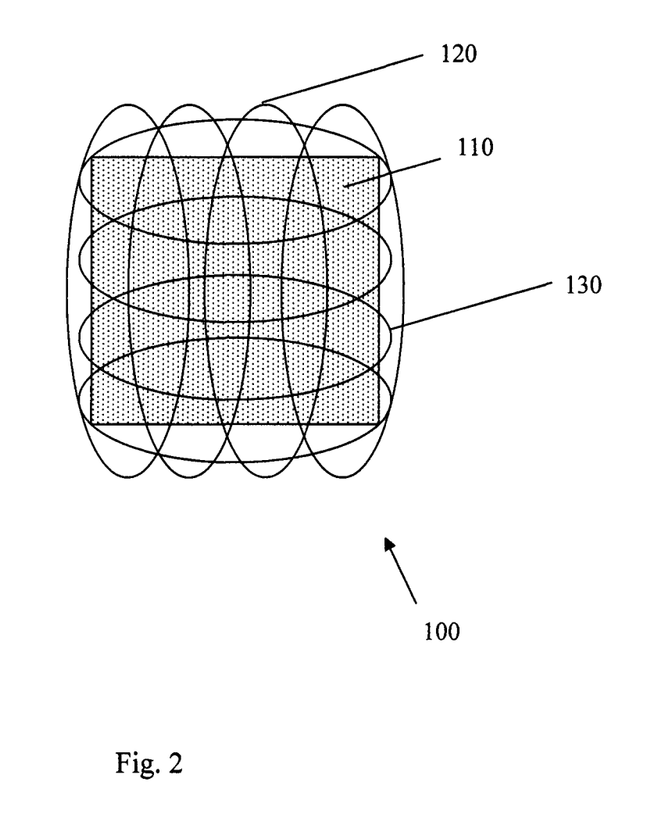
FIG. 2 is a simplified schematic view a completed flux-generating portion of the push-pull actuator.

After coil 120, a second coil 130 may be wrapped around the core 110 and coil 120. Coil 130 may be disposed approximately perpendicularly to coil 120, in order to produce flux in the orthogonal direction. Coil 130 may be made using similar or identical process steps to coil 120. This completes the fabrication of the flux-generating portion 100. FIG. 2 shows a schematic illustration of the completed device 100.

Alternatively, thin film fabrication techniques may be used to fabricate the flux-generating portion 100. In this case, the coil is deposited by depositing a conductive material in the appropriate locations on a substrate, then depositing the permeable core, then depositing another quantity of conductive material to form the coil. Each flux-generating portion may then be separated from the fabrication substrate by dicing, etc. Such fabrication techniques are described more fully in the incorporated '162 application, and explained further herein.

Figure 3A:
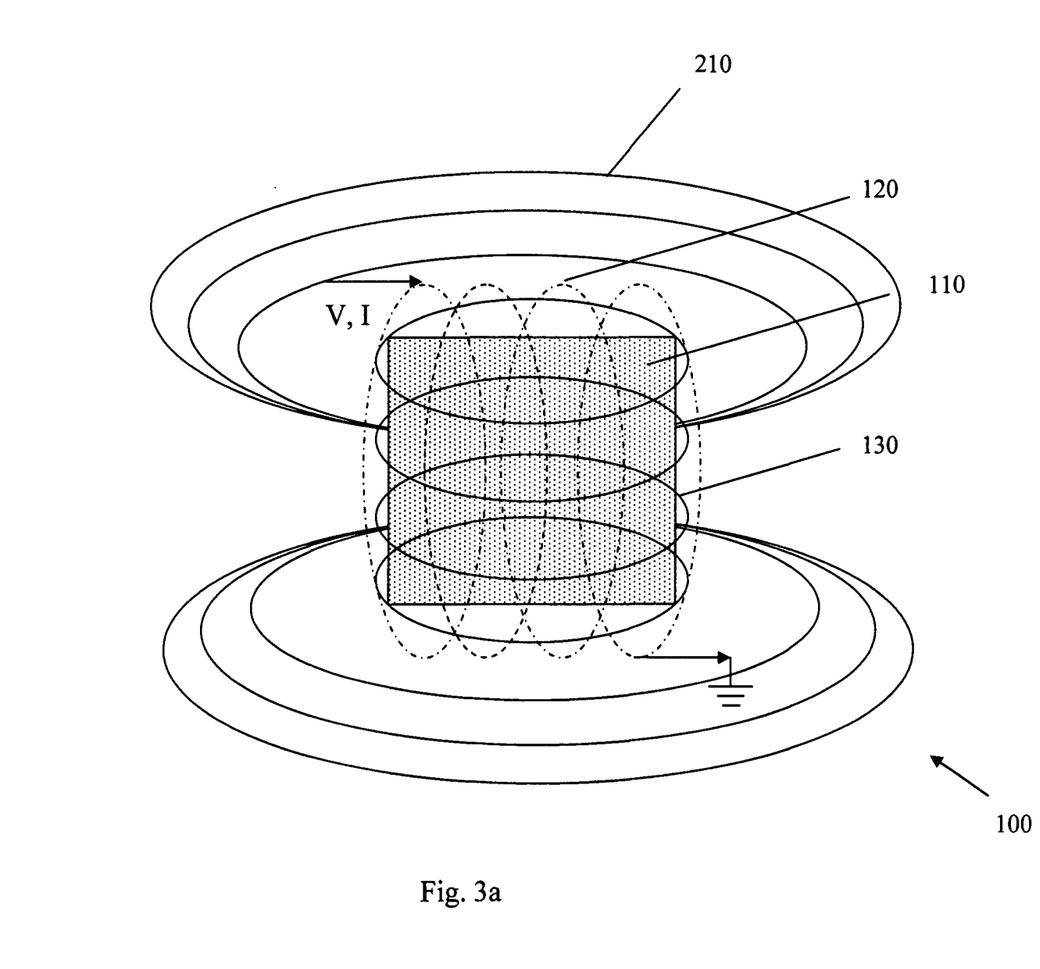
FIG. 3a is a simplified schematic diagram of the flux lines of the magnetic field produced by the flux generation portion of the push-pull actuator with one set of coils energized.
Figure 3B:
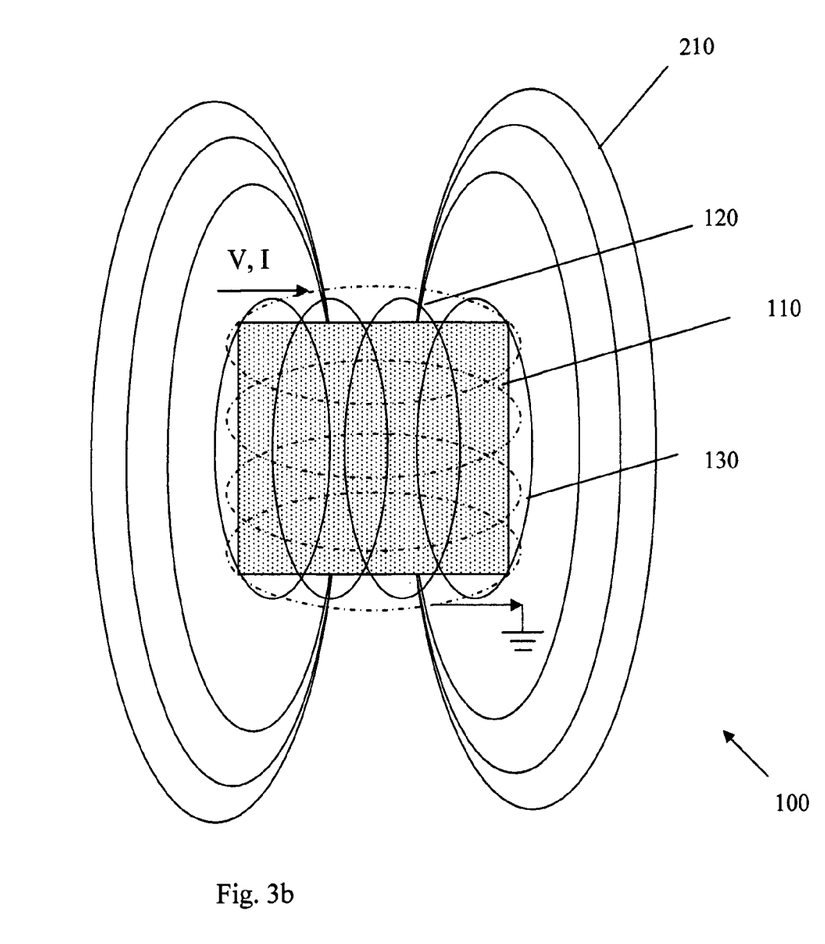
FIG. 3b is a simplified schematic diagram of the flux lines of the magnetic field produced by the flux generation portion of the push-pull actuator with a second, orthogonal set of coils energized.

FIGS. 3a and 3b illustrate the operation of the flux-generating portion 100. In FIG. 3a, coil 120 is energized, producing a magnetic field in the direction shown in the figure. In FIG. 3b, coil 120 is quiescent, and coil 130 is energized. Coil 130 produces a magnetic field substantially in the orthogonal direction as shown. As used herein, the word "substantially in a given direction" should be understood to mean that the major vector component of the force is along the given direction. Accordingly, a "substantially orthogonal direction" would be a direction wherein the major vector component is orthogonal, so that the substantially orthogonal direction is at least 45 degrees from the reference direction. The term "substantially different direction" should be understood to mean a direction at least about 45 degrees from a reference direction. For anti-parallel, or push-pull motions, the pulling motion should be understood to be a substantially different direction from the pushing motion, wherein the pulling motion direction is 180 degrees from the pushing motion direction.

Figure 3C:
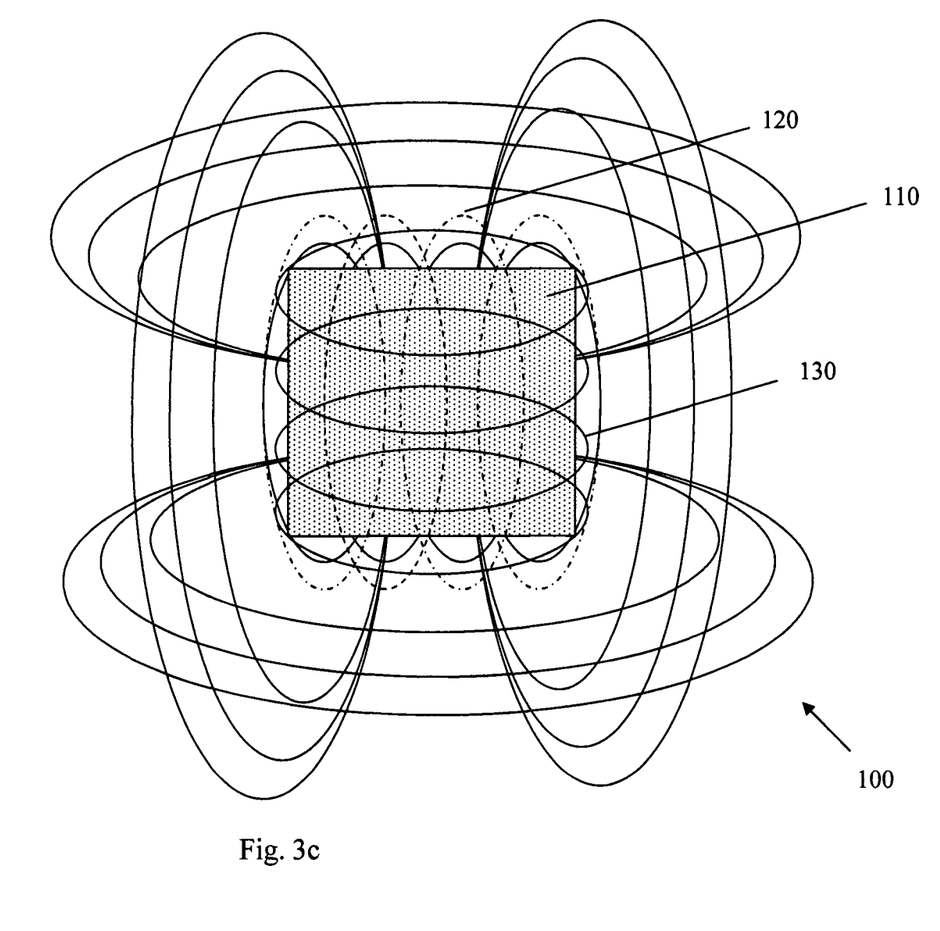
FIG. 3c is a simplified diagram of the flux lines produced by both sets of coils energized simultaneously.

FIG. 3c illustrates the fields generated when both coil 120 and coil 130 are energized simultaneously. By the law of superposition, the total effective field would be the vector addition of the field lines shown in FIG. 3c. As discussed further below, this may increase the off-axis force which may be advantageous in certain situations.

Figure 4A:
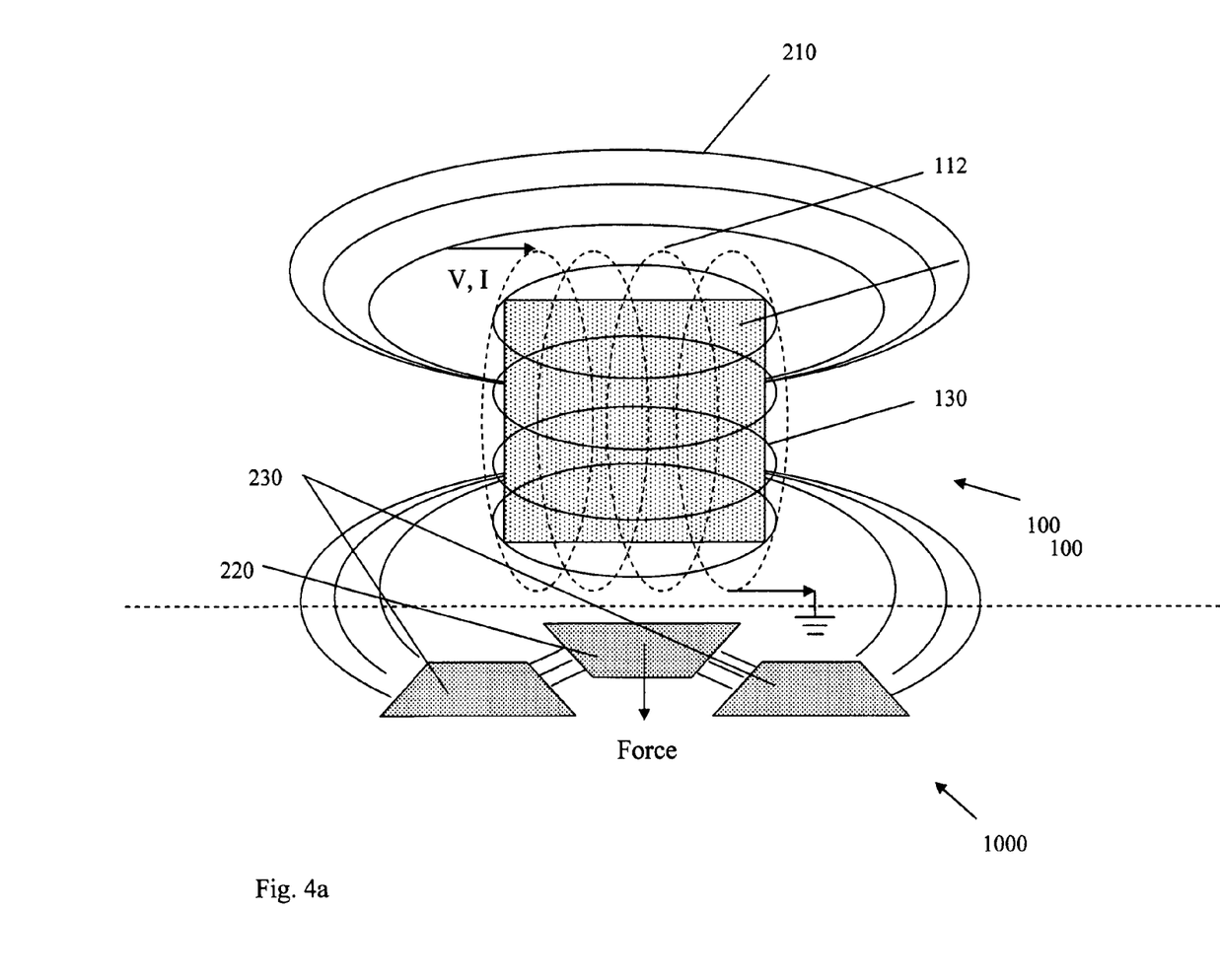
FIG. 4a is a simplified schematic view showing the interaction of the magnetic field with permeable magnetic portions the push-pull actuator, with the flux pushing the movable portion away from the flux-generating portion.

FIG. 4a shows the flux-generating portion 100 brought adjacent to a movable portion 1000. The dashed line between flux-generation portion 100 and movable portion 1000 indicates that these structures may be separate, or at least separable, although this separation is not required. The flux-generating portion 100 and the movable portion 1000 may also be mounted to or fabricated on the same surface, and thus not separable.

As shown in FIG. 4a, the movable portion 1000 may contain a plurality of magnetically permeable stationary features 230 and at least one permeable, but movable feature 220. The permeable movable feature 220 may have the permeable material embedded or inlaid in a movable structure, which is designed to move relative to the substrate on which it is manufactured. For clarity of illustration, only the permeable movable feature 220 is shown in FIG. 4, but it should be understood that this drawing is conceptual, and in actuality, the permeable movable feature 220 would be supported by a movable structural element. The movable structural element may be, for example, a cantilever or a hinge attached to a movable feature. Manufacturing methods and designs for such movable features with inlaid magnetic materials are described in further detail in U.S. Pat. No. 6,838,056, U.S. Pat. No. 7,229,838 and U.S. Pat. No. 7,622,783, each incorporated by reference in their entireties.

The stationary permeable features 230 may serve to shape the magnetic field produced by the flux-generating portion 100 in a way that efficiently causes the movable portion 220 to move toward the stationary features 230. For example, the stationary features 230 serve to collect the field lines of the magnetic field and focus them into the gap between the stationary features 230. The permeable movable magnetic feature 220 can reduce the overall energy of the system by moving into this area of concentrated field lines, thereby reducing the reluctance of the path of the field lines. Accordingly, a force arises on the permeable movable feature 220, causing in to move toward the stationary features 230 and away from the flux-generating portion 100, in order to reduce the energy of the system. Although shown as trapezoidal in FIG. 4a, this embodiment is exemplary only, and the shapes of the permeable features may be other trapezoidal, rectangular, curved or complex, computer-generated shapes. It should also be noted that the structures shown in FIGS. 4a and 4b are not necessarily to scale.

Figure 4B:
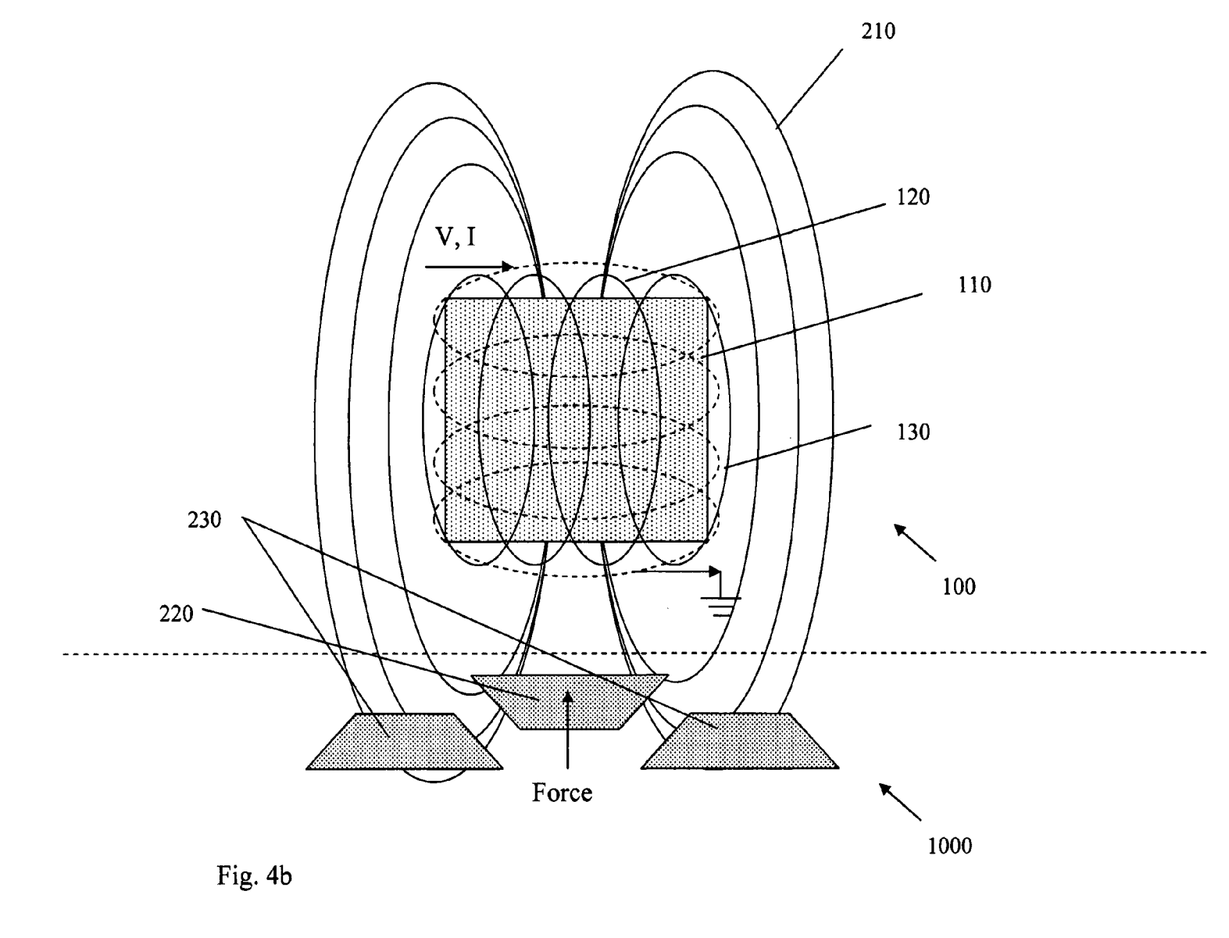
FIG. 4b is a simplified schematic view showing the interaction of the magnetic field with permeable magnetic portions the push-pull actuator, with the flux pulling the movable portion toward the flux-generating portion.

In FIG. 4b, the first coil 120 is quiescent, and the second coil 130 is energized. This produces a magnetic field along the axis of coil 130 as shown in the figure. Because of the geometry of the device, the field lines become more concentrated as they approach and re-enter the permeable core 110, producing a field gradient in this region. Accordingly, the permeable movable feature 1330 can reduce the energy of the system by moving toward the area of concentrated field lines near the flux-generating portion 100. This effect produces the "pulling" motion of the permeable feature 220 toward the flux-generating portion 100, which is in the opposite direction of the "pushing" motion depicted in FIG. 4a. By combining the motions shown in FIGS. 4a and 4b, by appropriate sequential energizing of coils 120 and 130, a back-and-forth, antiparallel or reciprocating motion can be induced in the movable permeable feature 220. When the movable permeable feature 220 is coupled to a shaft or other structural element, it may cause this structural element to move accordingly.

Figure 5:
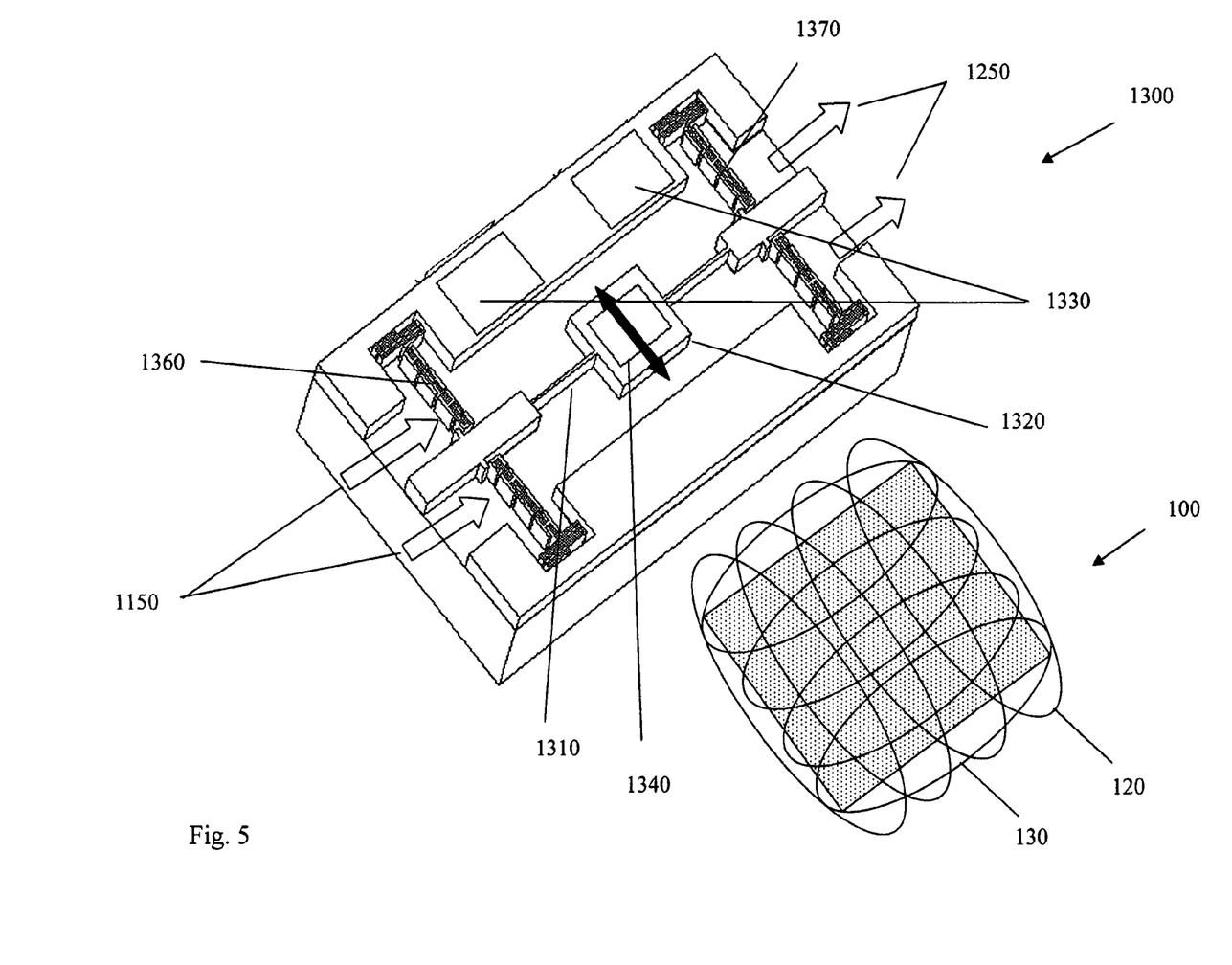
FIG. 5 is a simplified schematic view of an exemplary MEMS pumping system using the exemplary electromagnetic pump of FIGS. 5 and 6, with passive valving mechanisms driving fluid from the reservoir to the output.

FIG. 5 is a simplified schematic perspective view of a push-pull MEMS electromagnetic actuator 100, 1300 in which the movable permeable feature is coupled to such a structural element. In the case shown in FIG. 5, the movable structural element is a diaphragm 1310 separating two fluid chambers in a fluid pump. As before, the pump may include a flux-generating portion 100 and a movable portion 1300. It should be understood that the structures shown in FIG. 5 are not necessarily drawn to scale, and that changes in the relative placement, shapes and sizes of the structures may be undertaken to optimize various behaviors of the device. FIG. 5 is given as an illustration of an application in which the push-pull actuator 100 may be placed.

One exemplary embodiment of the device 1300 may use a movable pumping element, member 1320 upon which a magnetically permeable material 1340 is formed or inlaid. The movable member 1320 may be connected to the walls of a fluid cavity by the flexible membrane or diaphragm 1310. The diaphragm 1310 may separate two fluid chambers, an upper chamber 1335 from a lower chamber 1336. It should be understood that the terms "upper" and "lower" are arbitrary distinctions, and do not depend on the orientation of the device 1300, but may instead be referred to as a "first" chamber and a "second" chamber. For clarity with reference to FIG. 5, the terms "upper" and "lower" will be used.

The a movable structure 1300 may include a plurality of valves 1360 and 1370, which allow a fluid to flow in one direction but resist flow in the opposite direction, when the flexible diaphragm moves. These valves 1360 and 1370 may allow the fluid to pass through the upper chamber 1335 in one direction only when the pump is activated. Another set of similar valves may be disposed in the lower chamber 1336. These valves may be active valves, or alternatively, they may be passive valves as shown in FIG. 5. The passive valves open and close in response to the fluid pressure generated by the pump. When positive pressure is exerted by the fluid and against the wall of the valve 1370 in the upper chamber 1335, output valve 1370 may open expelling fluid from the upper chamber 1335. The wall of the valve may be attached to the substrate by a region of flexible material creating a hinge, such that the wall may bend about the hinge. A lip, step or other mechanical détente may prohibit the valves 1360 and 1370 from opening in the opposite direction in response to a change in direction of the flow. When negative pressure (suction) is exerted on the fluid in the upper chamber, input valve 1360 may open, drawing fluid into the upper chamber 1335, while output valve 1370 remains shut against the lip or step.

The push-pull MEMS electromagnetic pump 100, 1300 may also have a set of stationary magnetic features 1330, which interact with the magnetic flux produced by the adjacent flux-generating portion 100, which will be more fully described below.

As before and as shown in FIG. 5, the flux-generating portion 100 may be a magnetically permeable material 110, such as a NiFe permalloy core, around which a plurality of coils 120, 130 of conductor is wound. As previously described, energizing coil 120 with a current causes a magnetic field to be generated along the axis of the coil, and energizing coil 130 causes a magnetic field to arise in the orthogonal direction.

When the flux-generating portion 100 is brought into proximity with the movable portion 1300, the flux will cross the gap between the substrates and enter the stationary features 1330 of the push-pull MEMS electromagnetic pump 1300. Because of the high permeability of stationary features 1320, the flux will be concentrated by these features, preferring to travel through this material rather than through the air surrounding them. The flux will then jump between the stationary features 1320, forming a region of concentrated flux therebetween, which will tend to draw the permeable material 1340 on the flexible diaphragm 1320 toward the stationary features 1330. Thus, activating the coil 120 will cause the upstroke of the movable portion, forcing fluid to be expelled from the upper chamber 1335. This same action will cause fluid to enter the lower chamber 1336 through its input valve.

For the downstroke of the pump, i.e. forcing fluid from the lower chamber and into the upper chamber, the orthogonal coil 130 may be used. When the orthogonal coil 130 is energized, the motion of the piston 1330 may be toward the flux-generating portion 100, as described previously with respect to FIG. 4b. This results from the concentration of flux lines re-entering the permeable core 110 as was illustrated in FIG. 4.

Thus, when the coil 120 is energized, the motion of the flexible diaphragm 1320 is away from the flux-generating portion 100 and toward the stationary poles 1330, as was previously described with respect to FIG. 4a. When coil 130 is energized, the motion of the flexible diaphragm 1320 is toward the flux-generating portion 100 and away from the stationary poles 1330, as was previously described with respect to FIG. 4b. Accordingly, by appropriate sequential energizing of coils 120 and 130, a back-and-forth, anti-parallel, reciprocating motion can be induced in the movable diaphragm 1330, thus pumping fluid through the device.

One advantageous feature of the design shown in FIG. 5 is that the fluidic region, i.e. the wet region containing the fluid to be pumped, is totally contained and not in fluid communication with the flux-generating means 100. This is made possible because the actuation mechanism is an action-at-a-distance type as previously described, such as electrostatic or electromagnetic forces generated by the flux-generating portion 100. This action-at-a-distance allows the wet region to be totally isolated from the flux-generating portion 100, and thus no leakage occurs and substantial head pressures can be generated.

Another benefit of the design illustrated in FIG. 5 is that the push-pull action of the pump does not completely rely on the restoring force of the diaphragm for the downstroke of the device. In the case of a similar device described in U.S. patent application Ser. No. 12/801,162, the pump relies on magnetic force to drive the up stroke and relies on the restoring force of the springs to drive the downstroke. To equalize the pressure created during the upstroke and downstroke the restoring force of the springs must be equal to half the maximum magnetic force. On the upstroke half the magnetic force will be converted into potential energy in the restoring springs and half will create the pressure to move the fluid. In this invention the total force creating the pumping pressure is the sum of the spring restoring force and the magnetic force when coil 130 is energized. This allows for much weaker springs to be used and thus increased the maximum pressure asserted on the fluid and thus increases the potential flow rate and output pressure of the pump. Both of there parameter are critical.

In addition to energizing coils 120 and 130 sequentially, they may be energized simultaneously as was illustrated in FIG. 3c. By the law of superposition, this may create a larger, off-axis magnetic field, which may be used to draw the movable portion in an off-axis direction, and/or with a greater force because of the greater concentration of flux lines with both coils energized. The energized coils can be oriented to either increase the force due to a high gradient as previously discussed or by the increasing the flux through the fixed and moveable magnetic materials thus increasing the force created. The increase in force created by energizing both coils would allow for the reduction in the size of the flux generating source 100 which is advantageous for the drug pump application described below, wherein the overall reduction in the device size reduces the intrusiveness of the device on the patient.

It may also be possible to actuate a movable portion in a third direction with both coils energized. In the orientation described previously, the flux generated by both coils will create opposing forces in the upstroke and downstroke direction. The sum of these forces may create a lower force in either the upstroke or downstroke direction. The device could be designed such that the opposing forces are equal and hence the device is held rigidly in place. This may have some advantages in the case where a three-position microactuator is required to resist motion in all three positions.

A device may also be designed wherein both coils 120, 130 are energized and a first actuator is held rigid and a second antiparallel actuator that requires a high off axis field level moves in an off-axis direction driven by the off-axis fields, accordingly.

It should be noted that although FIG. 5 has the fluid flowing from the upper chamber 1335 and lower chamber 1336 in the same direction, they may also be configured to pump in antiparallel directions, by changing the angles of the passive valves. This may be convenient for applications needing antiparallel flows, for example, in a situation needing more than one therapeutic agent to be delivered to a patient simultaneously.

A number of applications of the push-pull electromagnetic actuator are envisioned. One exemplary application is as a low-dosage delivery mechanism for a therapeutic substance into the body of a patient in need of that substance. In this application, the push-pull actuator may be deployed as a pump, and may be coupled to a drug reservoir 700 and a cannula 800 to deliver the therapeutic substance, as shown in FIG. 6.

In this application, the pushpull actuator may pump a therapeutic substance from a storage reservoir 1100 to an output orifice 1200. The output orifice 1200 may be, for example, a subdermal cannula or needle.

A drug reservoir 500 may hold a volume of the therapeutic substance, which is pumped into the patient according to his needs, or according to a predetermined schedule, or according to a profile stored in the memory of a microprocessor 900. The cannula 800 may be a transdermal needle, which delivers the therapeutic substance to a layer of tissue under the skin 820, such as muscle or fat. The location of the cannula 800 and its depth may depend on the therapy being applied. For example, in the case of diabetic patients, the drug reservoir 500 may be filled with insulin, and the cannula 800 may deliver the insulin from the drug reservoir 500 to a subcutaneous region in the patient. The insulin may be forced to flow from the reservoir 500 through the cannula 800 by the microfabricated pump 400. In one exemplary embodiment, the microfabricated pump is the push-pull MEMS electromagnetic pump shown in FIG. 5. The operation of the pump 400 may be under the control of the microprocessor 900, according to a preset schedule 910, or according to input from the patient, or in response to another device 700 which may be a biochemical sensor which is responsive to a condition of a patient, and generates a signal indicative of that condition. In one embodiment, the sensor may detect the presence of, the absence of or the level of some compound, and activate the microfabricated pump 400 accordingly, in response to this measurement.

Figure 6:
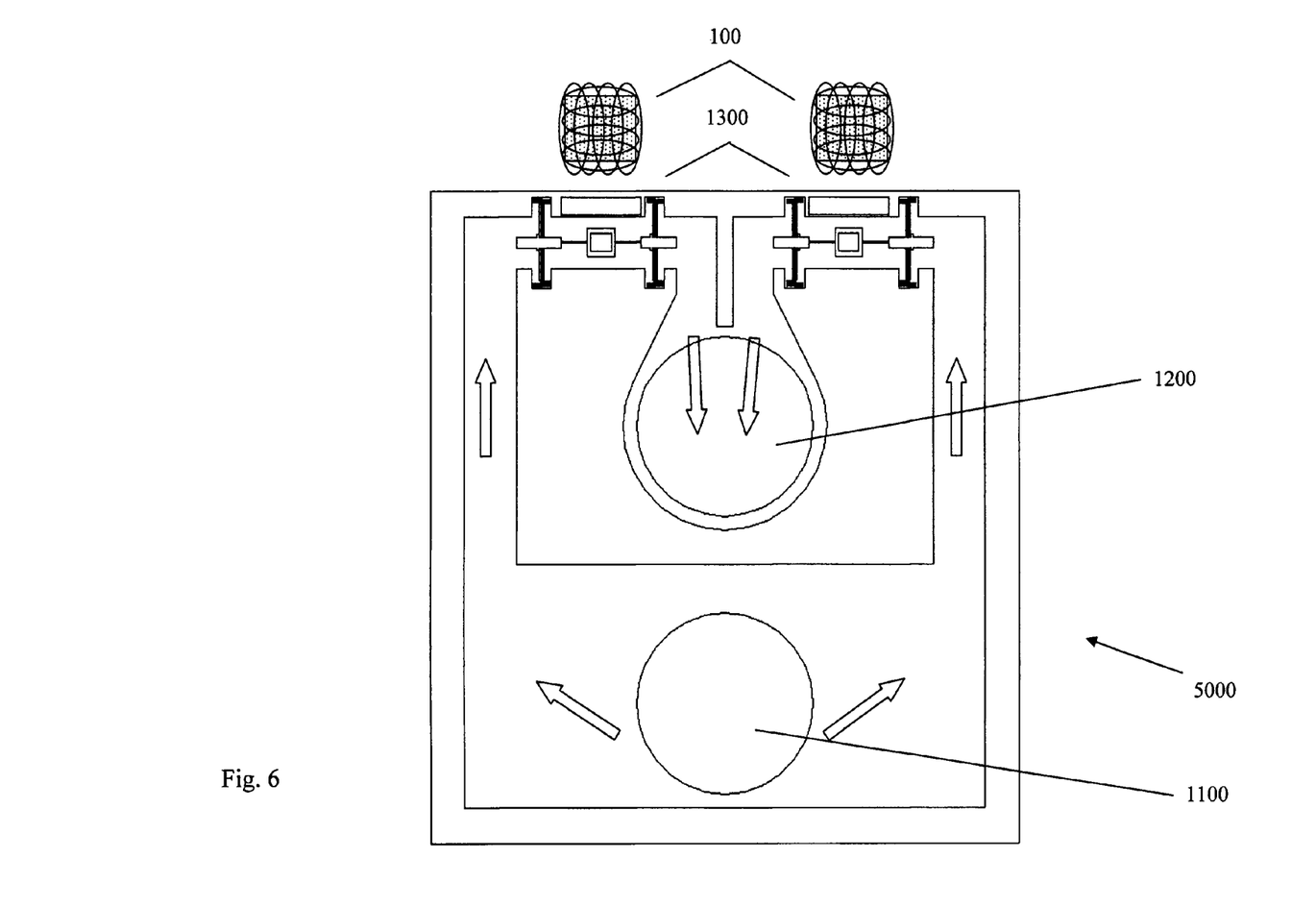
FIG. 6 is a simplified schematic view of the push-pull MEMS electromagnetic pump of FIG. 5 configured as a drug delivery system, by coupling one or more push-pull MEMS electromagnetic pumps with an input and output orifice.
Figure 7:
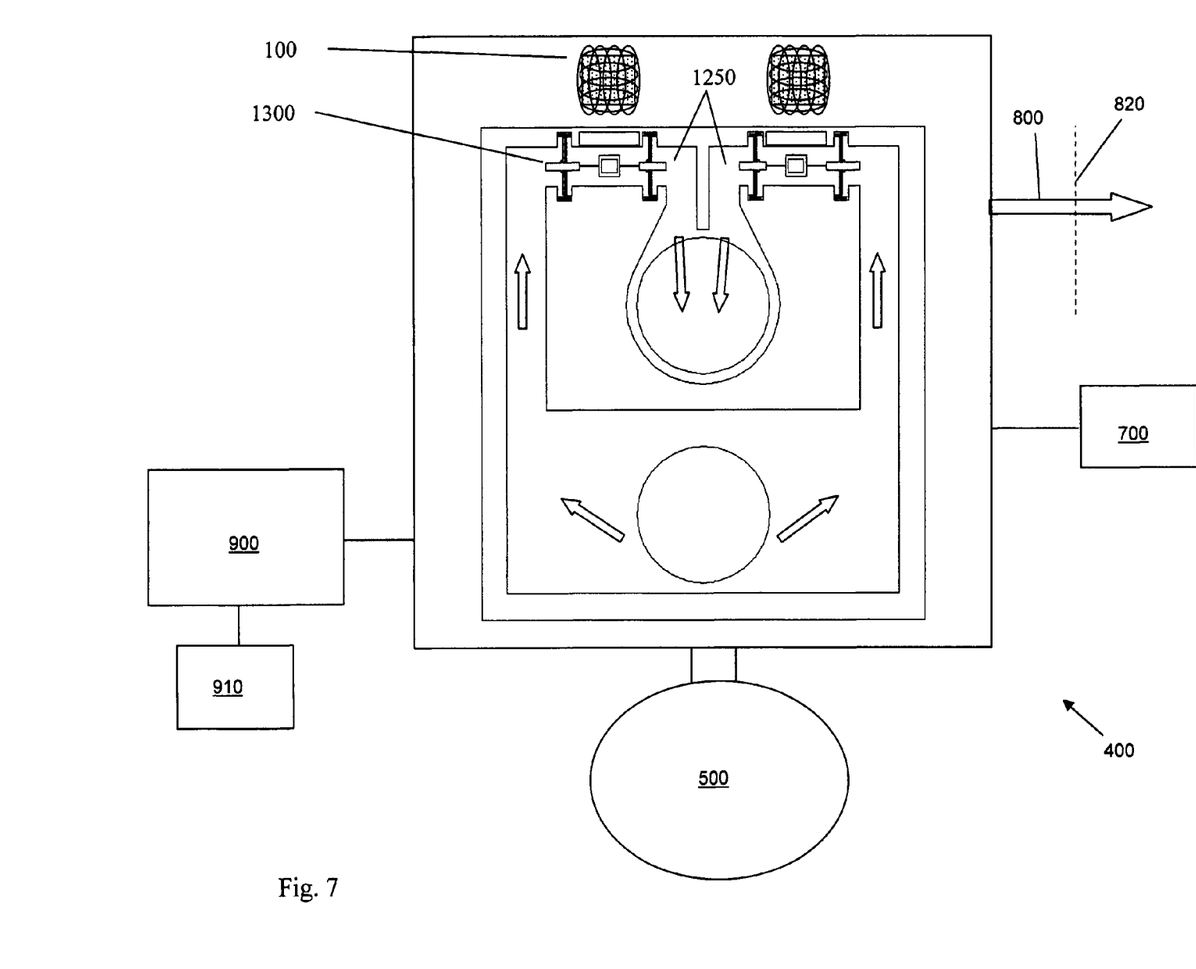
FIG. 7 is a simplified schematic view of the push-pull MEMS electromagnetic pump of FIG. 5 configured as a drug delivery system, by coupling the push-pull MEMS electromagnetic pump with a drug reservoir and cannula.

When the drug delivery system illustrated in FIG. 6 is configured to deliver insulin to a diabetic patient, for example, the drug reservoir may contain about 300 units of insulin, enough to provide about 10 days worth of the drug to a diabetic patient. The pumping volume of the push-pull electromagnetic MEMS pump described above may be about 0.5 nl. Theoretical models predict that the magnetic field generates enough force to draw the diaphragm down within about 200 μsec, and pulling it back to its original position in about the same time, depending on the viscosity of the fluid and other design choices. Thus, a pumping speed of up to 150 μl/min could theoretically be achieved using the designs described above. However, to allow for some leakage, viscosity effects and other losses, a pumping rate of about 60 μl/min may be readily achievable. At this pumping rate, a 10 unit dose of insulin would take about 1.6 minutes to administer. Of course, instead of a single administration, this dosage could be administered slowly or over several hours by activating the pump only for short intervals, or at a lower cycle rate. Assuming three such dosages per day, a patient may operate the pump on an SR41-type button battery for about 10.5 days before replacing the battery, consistent with the capacity of the drug reservoir. Conveniently, the presently marketed insulin pumps and pens have insulin-containing storage cartridges that need to be replaced every 3-30 days, so that replacement of components or containers on this time interval is familiar to most diabetic patients.

The description will now turn to fabrication of the actuator devices shown in FIGS. 1-6. Although the designs shown in FIGS. 5 and 6 may appear complicated, their fabrication is straightforward because all the complexity occurs in the same plane. The magnetically permeable features 1320 and 1330 first may be created by depositing a permeable material such as nickel-iron permalloy into a cavity of the appropriate shape previously created in the device layer of a silicon-on-insulator (SOI) substrate. For example, the permalloy may be deposited using well-known electroplating techniques. The resulting permeable feature may then be planarized using, for example, chemical-mechanical planarization (CMP). The complex shape of the shaft, pumping element and restoring springs may then be easily created in a single step by, for example, deep reactive ion etching of the shape in the device layer. These movable features may be released from the substrate by etching the underlying oxide layer of the SOI substrate. Techniques for accomplishing these steps are described more fully in U.S. Pat. No. 6,838,056, U.S. Pat. No. 7,220,594, and U.S. Pat. No. 7,229,838, each of which is incorporated by reference herein in its entirety. The fluid path may be sealed by bonding a top wafer to the actuator wafer to form the MEMS pump wafer. This top wafer may be any convenient material, such as silicon, glass, quartz or ceramic. The bonding material may be any adhesive substance that can maintain a fluid seal, such as a metal, epoxy or frit adhesive. Through wafer apertures may be formed in this lid wafer either before or after bonding, to provide fluid access to the input or output channels.

The flux-generating portion 100 may be formed on a separate or separable surface 100, as shown in FIG. 5. This may decrease the overall cost of the pump chip, as compared to microfabricating both components, the flux-generating portion 100 as well as the movable portion 1000. The coils 120 and 130 may simply be hand wound around a substantially square piece of permeable material 110.

Alternatively, the flux-generating portion may be fabricated on a motor substrate by first depositing the permeable cores 110 on the surface of the substrate. A seed layer may then be deposited over the permeable cores and covered with photoresist. The photoresist may then be patterned to create a stencil for the plating of the copper coils. The coils are then plated in the stencil and the stencil subsequently removed. Details as to the deposition of the permeable material, deposition of the seed layer, deposition and patterning of the photoresist and plating of the copper coils, is well known in the art or described in further detail in the '056, '594 or '838 patents and thus will not be described further herein. It should be understood that electroplating of the copper coils is only one exemplary method, and that other methods may be used to form the coils, such as ion beam deposition, ion milling and lift-off methods.

The motor substrate may then be coupled to the actuator substrate by any convenient mechanism, such as glues, cements or epoxies, or may simply be held in close proximity by a positioning stage, for example. The bond need not be hermetic or even watertight, as it does not seal fluid. It is recommended, however, that the bond maintain a close proximity between the permeable cores of the motor substrate and the permeable features of the actuator substrate, in order to obtain efficient coupling of the magnetic flux into the actuator substrate. Typically, maintaining a separation of less than about 2 microns is sufficient.

In the drug delivery application, the fluid input and output lines may be capillary tubing made of polyimide jacketed quartz or a polymer material such as polyetheretherketone (PEEK) which may be several hundred microns in diameter. These fine tubes may, in turn, be glued to the orifices of the MEMS pump wafer using, for example, a two-part 5-minute epoxy, or any of a number of other suitable adhesives. Using tubing bores and channels of 20 μm to 100 μm, it is clear that this apparatus is capable of delivering slurry-based therapeutic substances which have particulates suspended in a conveying fluid, as well as pure fluid-based substances.

There are a number of other applications for the push-pull electromagnetic MEMS actuator in addition to the fluid pump described above. Other situations are envisioned where a push-pull mechanism is desirable. Other such application includes micromechanical pistons that cause reciprocating movement on a member. Another application may be a sensor where back-and-forth motion is needed.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. While the embodiment described above relates to drug delivery systems, it should be understood that the techniques and designs described above may be applied to any of a number of other devices, such as valves, pistons and other movable devices. Furthermore, although embodiments are described each with a certain combination of features, it should be understood that any of a number of other embodiments are envisioned, which may have different combinations of features. Finally, details related to the specific design features of the push-pull electromagnetic MEMS pumps, such as coil number and dimensions, are intended to be illustrative only, and the invention is not limited to such embodiments. Accordingly, the exemplary implementations set forth above, are intended to be illustrative, not limiting.

What is claimed is:

1. An microfabricated electromagnetic actuator, comprising:
   a movable structure formed on a substrate with at least one magnetically permeable, movable feature;
   a flux-generating mechanism, wherein the flux-generating mechanism generates lines of flux which are collected by the at least one magnetically permeable feature, wherein the flux-generating portion includes a plurality of electrical coils, each of which generates a magnetic field in a substantially different direction, wherein the fields produced by the plurality of coils causes a movement of the movable structure in a plurality of substantially different directions.

2. The microfabricated electromagnetic actuator of claim 1, wherein the flux-generating portion is separate from the substrate and further comprises a single magnetically permeable core, around which the plurality of coils is wound.

3. The microfabricated electromagnetic actuator of claim 1, wherein the movable structure comprises a magnetically permeable feature disposed on a flexible diaphragm separates two fluidic chambers.

4. The microfabricated electromagnetic actuator of claim 3, wherein the flux-generating portion comprises two electrical coils wound about two axes, wherein the axes are substantially perpendicular to one another.

5. The microfabricated electromagnetic actuator of claim 4, further comprising two stationary permeable magnetic structures, which are shaped to focus the lines of flux in the gap between the two stationary permeable magnetic features, wherein the at least one magnetically permeable, movable feature interacts with the focused lines of flux in the gap.

6. The microfabricated electromagnetic actuator of claim 5, wherein the magnetically permeable, movable feature is configured to move toward or away from the stationary permeable magnetic structures, upon activation of at least one of the plurality of electrical coils.

7. The microfabricated electromagnetic actuator of claim 6, wherein the a movable structure includes a plurality of valves, which allow a fluid to flow in one direction but resists flow in the opposite direction, when the flexible diaphragm moves.

8. The microfabricated electromagnetic actuator of claim 7, wherein the valves are passive valves, each having a rigid wall hingedly attached to a rigid substrate, wherein the hinged attachment bends in response to fluidic pressure against the rigid wall.

9. The microfabricated electromagnetic actuator of claim 8, wherein the valve move in one direction in response to fluid pressure, but are prevented from moving in another direction by a mechanical détente.

10. The microfabricated electromagnetic actuator of claim 5, wherein the magnetically permeable, movable feature and the two stationary magnetically permeable structures all comprise an alloy of nickel and iron.

11. The microfabricated electromagnetic actuator of claim 3, wherein when the flexible diaphragm moves in one direction, fluid is forced to flow through one fluid chamber, and when the flexible diaphragm moves in another direction, fluid is forced to flow through the other chamber.

12. A system for delivering a therapeutic substance to a patient, comprising:
   a reservoir containing a volume of the therapeutic substance;

a cannula that delivers the therapeutic substance to a region beneath an outer layer of skin of the patient; and a microfabricated fluid pump using the microfabricated electromagnetic actuator of claim 1, wherein the microfabricated fluid pump is configured to pump the therapeutic substance from the reservoir through the cannula to the patient, wherein the microfabricate fluid pump pumps the therapeutic substance in a plane substantially parallel to the substrate.

13. The system of claim 12, further comprising:

a microprocessor which controls the microfabricated fluid pump, and operates the pump according to at least one of: an algorithm stored in a memory, the commands of a user, and a signal from a biochemical sensor.

14. The system of claim 12, further comprising:

a sensor coupled to the microprocessor, wherein the sensor is responsive to a condition of the patient, and generates a signal indicative of that condition.

15. The system of claim 12, further comprising:

a power source which powers the microfabricated fluid pump.

16. The system of claim 12, wherein the microfabricated fluid pump uses a plurality of fluid valves moving substantially in the plane of the substrate, to move the therapeutic substance.

* * * * *